United States Patent [19]

Dewhurst et al.

[11] Patent Number: 5,718,231
[45] Date of Patent: Feb. 17, 1998

[54] LASER ULTRASOUND PROBE AND ABLATOR

[75] Inventors: Richard James Dewhurst, Poynton; Peter Alfred Payne, Bramhall; Qing Xin Chen, Hale; Kok Fu Pang, London, all of England

[73] Assignee: British Technology Group Ltd., London, England

[21] Appl. No.: 557,175

[22] PCT Filed: Jun. 14, 1994

[86] PCT No.: PCT/GB94/01276

§ 371 Date: Dec. 20, 1995

§ 102(e) Date: Dec. 20, 1995

[87] PCT Pub. No.: WO94/28804

PCT Pub. Date: Dec. 22, 1994

[30] Foreign Application Priority Data

Jun. 15, 1993 [GB] United Kingdom ............... 9312327

[51] Int. Cl.$^6$ ............................................. A61B 8/00
[52] U.S. Cl. ........................... 128/662.06; 128/662.03
[58] Field of Search ........................ 128/662.06, 662.03

[56] References Cited

U.S. PATENT DOCUMENTS

| | | | |
|---|---|---|---|
| 4,887,605 | 12/1989 | Angelsen et al. | 128/662.06 |
| 5,163,432 | 11/1992 | Ueno et al. | |
| 5,254,112 | 10/1993 | Sinofsky et al. | 128/662.06 |

FOREIGN PATENT DOCUMENTS

| | | |
|---|---|---|
| 329 392 | 8/1989 | European Pat. Off. . |
| 3082482 | 4/1991 | Japan . |
| 3131247 | 6/1991 | Japan . |
| 2212920 | 8/1989 | United Kingdom . |
| 92/07623 | 5/1992 | WIPO . |
| 92/16140 | 10/1992 | WIPO . |

OTHER PUBLICATIONS

Salimbeni, "Shock Wave Models Keep Laser Surgeons on Target", OLE, Jun. 1994, pp. 37–39.

(List continued on next page.)

*Primary Examiner*—Marvin M. Lateef
*Assistant Examiner*—Derrick Fields
*Attorney, Agent, or Firm*—Cushman, Darby & Cushman IP Group of Pillsbury Madison & Sutro LLP

[57] ABSTRACT

A laser ultrasound probe, suitable for intravascular use, of the kind having an ultrasonic transducer element comprising an ultrasound receiving surface of piezoelectric polymeric material and an optical fiber with one end directed forwardly from that surface and arranged to receive laser radiation for transmission through the optical fiber and emission from the said one end thereof, wherein the optical fiber is coupled with laser source means adapted to provide alternatively a relatively low average power laser beam, which, when modulated or pulsed and emitted from the one end of the optical fiber and incident on a target, will generate ultrasound at an intensity suitable to be received by the transducer element and converted thereby into electrical monitoring signals, and a relatively high average power laser beam suitable, when incident on the said target, to produce ablation thereof, the transducer element being sufficiently robust to withstand the ultrasound which is then also generated. The relatively low average power laser beam may alternatively be at a first wavelength which, when modulated or pulsed and emitted from the one end of the optical fiber into a medium which is highly absorptive at that wavelength, will cause said medium to generate and propagate ultrasound at an intensity suitable to be reflected by a target contacted by said medium and received by the transducer element and converted thereby into electrical monitoring signals, the relatively high average power laser beam being then at a second wavelength at which the said medium is transmissive and being suitable, when incident on the said target, to produce ablation thereof, the transducing element being sufficiently robust to withstand the ultrasound which is then also generated.

6 Claims, 5 Drawing Sheets

OTHER PUBLICATIONS

Crazzolara, "Analysis of the Acoustic Response of Vascular Tissue Irradiated by an Ultraviolet Laser Pulse", J. Appl. Phys. 70(3), 1 Aug. 1991, pp. 1847–1849.

White, "Intravascular Ultrasound Guided Holmium: YAG Laser Recanalization of Occluded Arteries", Lasers in Surgery and Medicine 12:239–245 (1992).

Dewhurst, "Developments in a Photoacoustic Probe for Potential Use in Intra–Arterial Imaging and Therapy", Acoustical Imaging, vol. 21.

Patent Abstracts of Japan, vol. 15, No. 252 (C–0844) Jun. 26, 1991, & JP,A,30 082 482 see abstract.

Patent Abstracts of Japan, vol. 15, No. 337 (C–0862) Aug. 27, 1991, & JP,A, 31 031 242 see abstract.

LASER ULTRASOUND PROBE AND ABLATOR

This application claims benifit of intenational application PCT/GB94/01276, filed Jun. 14, 1994.

BACKGROUND OF THE INVENTION

1. Field of the Invention

This invention relates to probes having a forward-looking ultrasound receiver and an optical fibre for directing laser signals to a target to generate ultrasound to be sensed by the ultrasound receiver, especially for use in intra-arterial imaging and, preferably, therapy.

2. Description of Related Art

It has been proposed, in a paper entitled "Analysis of the acoustic response of vascular tissue irradiated by an ultraviolet laser pulse" by H. Crazzolara et al. (J. Appl. Phys. 70 (3), 1847–9, 1991), to use an ultrasound probe having a disc of a piezoelectric polymer, specifically polyvinylidene fluoride (PVDF), supported on an end of a metal rod element, to monitor the ultrasound generated during oblation of a target by incidence upon it of laser beam pulses emitted from an end of an optical fibre which is physically separate from the ultrasound probe, thereby to distinguish between incidence of the laser pulses on normal arterial wall material and on calcified hard tissue of a sample of arterial material being investigated in vitro.

Probes of the general kind to which the present invention relates have also previously been described, in UK Patent Specification No. 2212920, which describes inter alia such a probe in which the ultrasound receiver has a dished circular transducer element of a piezoelectric polymer material such as PVDF, and an optical fibre projects coaxially through the centre of the transducer element and has an end, in front of the transducer element, from which laser beam pulses are emitted in use of the apparatus to strike a target, preferably at a focus of the dished transducer element, causing it to emit laser-induced ultrasound signals which are received by the transducer element, thus enabling the target to be investigated ultrasonically.

SUMMARY OF THE INVENTION

It is an object of the present invention to provide an improved laser ultrasound probe, suitable for intravascular use, of the kind having an ultrasonic transducer element having an ultrasound receiving surface of piezoelectric polymeric material and an optical fibre with one end directed forwardly from that surface and arranged to receive laser radiation for transmission through the optical fibre and emission from the the one end thereof.

According to one aspect of the invention, the optical fibre of such a probe is coupled with a laser source adapted to provide alternatively a relatively low average power laser beam which, when modulated or pulsed and emitted from the one end of the optical fibre and incident on a target, will generate ultrasound at an intensity suitable to be received by the transducer element and converted thereby into electrical monitoring signals, and a relatively high average power laser beam suitable, when incident on the said target, to produce ablation thereof, the transducer element being sufficiently robust to withstand the ultrasound which is then also generated.

According to another aspect of the invention, the optical fibre of such a probe is coupled with a laser source adapted to provide alternatively a relatively low average power laser beam at a first wavelength which, when modulated or pulsed and emitted from the one end of the optical fibre into a medium which is highly absorptive at that wavelength, will cause the medium to generate and propagate ultrasound at an intensity suitable to be reflected by a target contacted by said medium and received by the transducing element and converted thereby into electrical monitoring signals, and a relatively high average power laser beam at a second wavelength at which the medium is transmissive and suitable, when incident on the target, produce ablation thereof, the transducing element being sufficiently robust to withstand the ultrasound which is then also generated.

In a particular form of this last-mentioned probe one end of the optical fibre is directed in a forward longitudinal direction of the probe and the ultrasonic transducer element is a forward looking transducer element of the probe, susceptible to ultrasound generated and propagated forwardly in the medium and reflected by a first target located in the forward direction. The probe is further provided with at least one sideways-looking ultrasonic transducer element susceptible to ultrasound generated and propagated in the medium and reflected by a second target contacted by the medium and disposed laterally of the probe. Preferably such a probe is provided with a plurality, say sixteen, of the sideways-looking transducer elements, disposed circumferentially around the probe and each having its own electrical output-signal connection for connection to signal processing apparatus for image derivation.

In any of the embodiments of the invention as referred to above, the one end of the optical fibre preferably projects through and forwardly from the ultrasound receiving surface.

BRIEF DESCRIPTION OF THE DRAWINGS

Preferred embodiments of an improved laser ultrasound probe according to the invention are described below with reference to the accompanying drawings, in which.

DETAILED DESCRIPTION OF THE PREFERRED EMBODIMENTS

Figure 1:
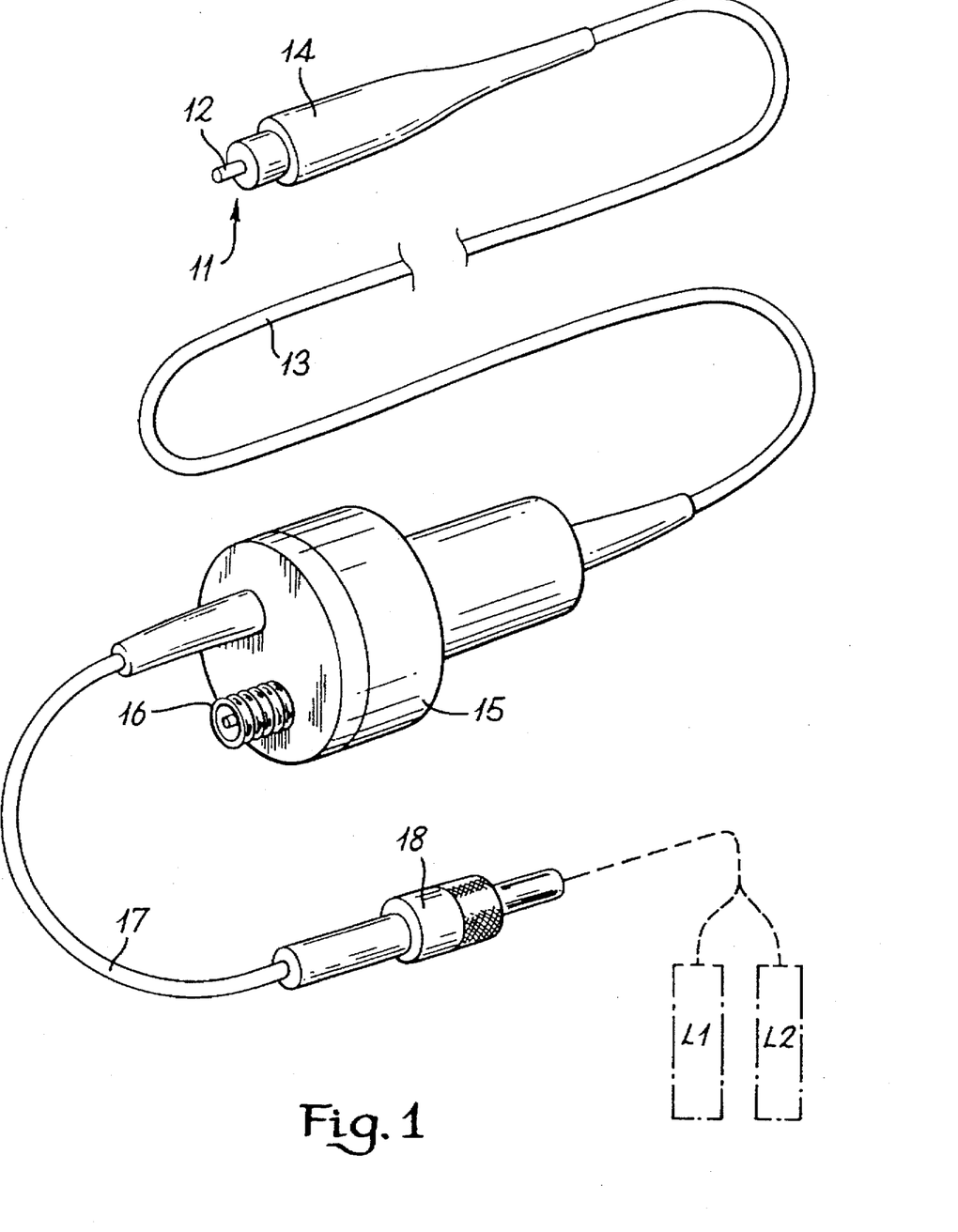
FIG. 1 is a general perspective view showing a probe according to the invention, together with a coupling element for coupling an optical fibre of the probe to laser source means and electrical output connections from a piezoelectric ultrasound transducer of the probe to an electrical receiver (not shown)

The probe shown in FIG. 1 has a probe head 11, from a front end face of which projects one end of an optical fibre (which may suitably be a PCS 600 optical fibre), and a cable 13 to which the probe head 11 is secured and through which extend the optical fibre 12 and an electrical connection from the probe head as will be described. The connection between the probe head 11 and the cable 13 may be covered and mechanically strengthened by the provision of a shrunk-on sleeve 14 of suitable plastic material, as shown in FIG. 1. At its other end, the cable 13 extends into a signal connector or manifold 15 which includes an electrical socket 16, for example a standard SMC socket, at which the electrical connection from the probe head 11 is terminated. The optical fibre 12 extends continuously through and beyond the manifold 15, and within a protective extension cable covering 17, to an optical fibre connector such as a standard SMA optical fibre connector. By means of the connector 18 the probe head 11 is connected to the output of a laser (not shown) operable selectively at either of two different output levels or (as shown schematically in FIG. 1) to the outputs of two lasers L1 and L2 each operable at a respective one of two different output levels. Thus the exposed end of the optical fibre 12 can be made to emit either lower average power pulses of laser light which, on striking a target, generate ultrasonic pulses which impinge on the probe head 14 and are converted into electric signals which appear at the socket 16 for processing in an ultrasonic investigation of the target, or higher average power laser pulses suitable to produce ablation of the target.

Figure 2:
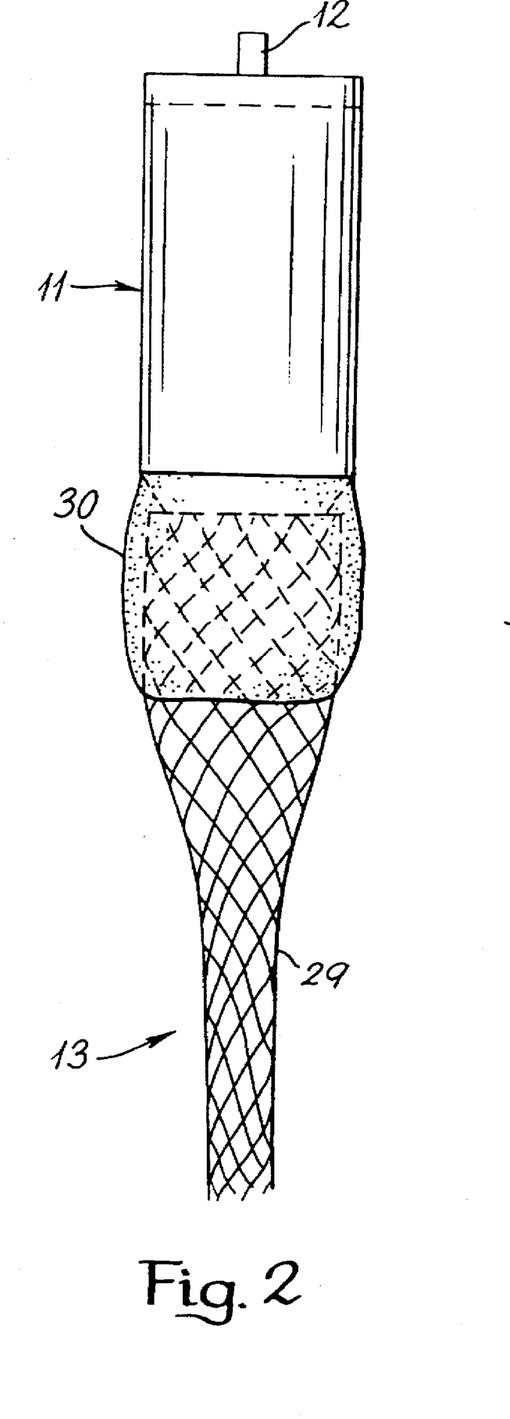
FIGS. 2 and 3 are respectively an elevational view and a longitudinal sectional view, both on a larger scale, of the probe shown in FIG. 1.
Figure 3:
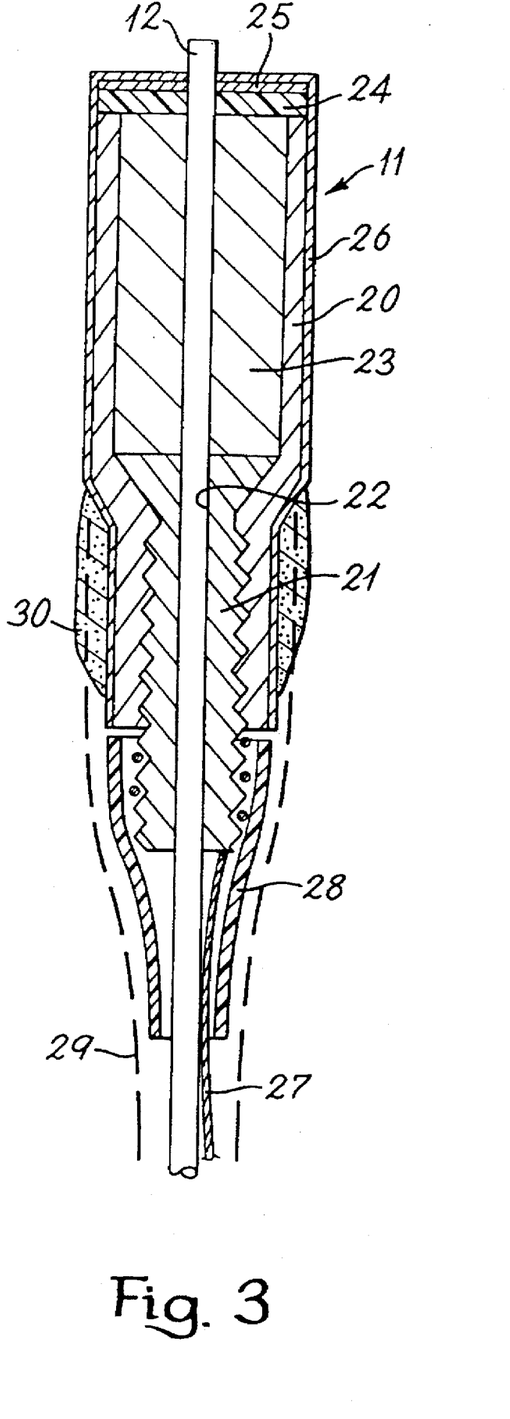

The probe head 11 shown in FIG. 1, and its connection to the cable 13, are shown on a larger scale and in detail FIGS. 2 and 3. The probe head 11, as best seen from FIG. 3, comprises a stepped cylindrical shell 20 of perspex or other suitable electrical insulating material, of which the smaller-diameter section is internally threaded to receive a brass or other conductive screw 21 with an axial bore 22 through which the optical fibre 12 extends. The interior of the larger-diameter section of the shell 20 is filled with a silver-loaded epoxy resin plug 23 (through which the optical fibre 12 also extends axially). The plug 23 and the surrounding edge of the shell 20 provide a support for a piezoelectric transducer element in the form of a superposed film 24 of a piezoelectric polymer, suitably PVDF, provided with a metallised surface film 25 on its surface remote from the plug 23. The piezoelectric film 24 is bonded with a suitable adhesive, for example cyanoacrylate, to the plug 23 and to the annular and of the shell 20 which ensures electrical isolation of the plug 23 from the metallised film 25. The film 25 is covered by a finishing surface layer 26 of silver conductive paint which also covers the outer surface of the shell 20.

The cable 13 has at its centre the optical fibre 12 and also includes an inner electrical conductor in the form of an enamelled copper wire 27 of which one end, stripped of its insulating enamel, is wrapped around the threads of the screw 21 where it is held in place by means of a shrunk-on heat-shrink sleeve 28. The cable 13 also includes an outer screening conductor formed by a braided copper sheath 29, and one end of this is secured by means of silver-loaded epoxy resin 30 to the conductive paint coating 26 of the shell 20.

Thus one surface of the PVDF film 24 is electrically connected by its metallic film layer 25, the conductive paint layer 26 (which also serves as an extension of the external screening) and the silver-loaded epoxy bond 30 to the outer conductor 29 of the cable, while the other surface of the film 24 is in contact with the silver-loaded epoxy plug 23 and is electrically connected through it and the screw 21 to the cable inner conductor 27; and the inner and outer conductors of the cable are connected respectively to the inner and outer contacts of the socket 16.

Figure 4:
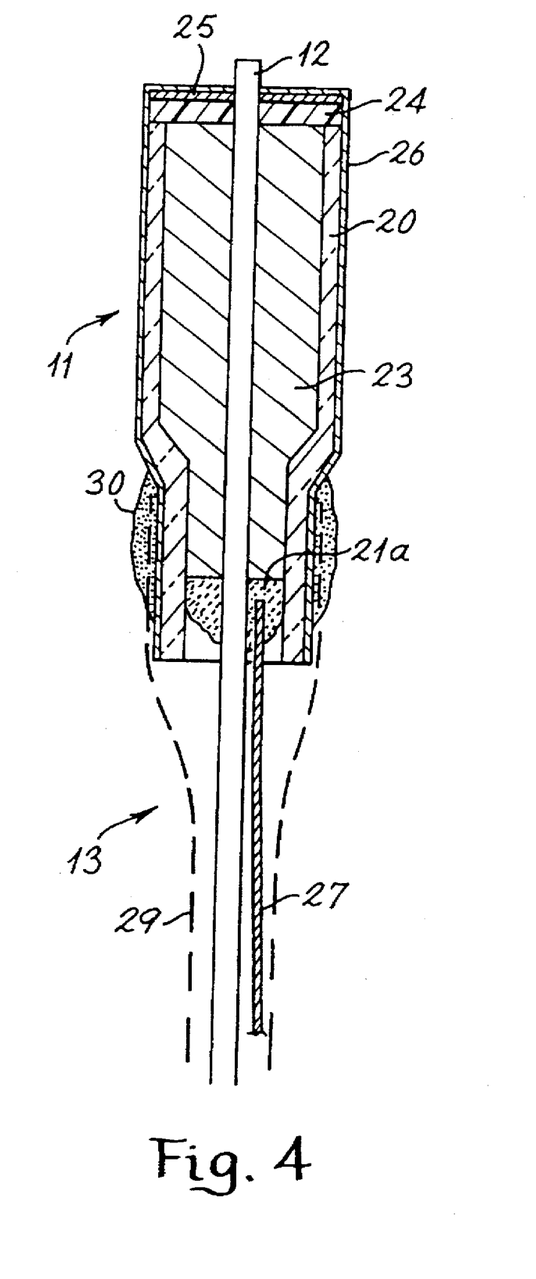
FIGS. 4 and 5 are longitudinal sectional views of two further embodiments of a probe according to the invention, incorporating minor constructional modifications of that shown in FIGS. 2 and 3.
Figure 5:
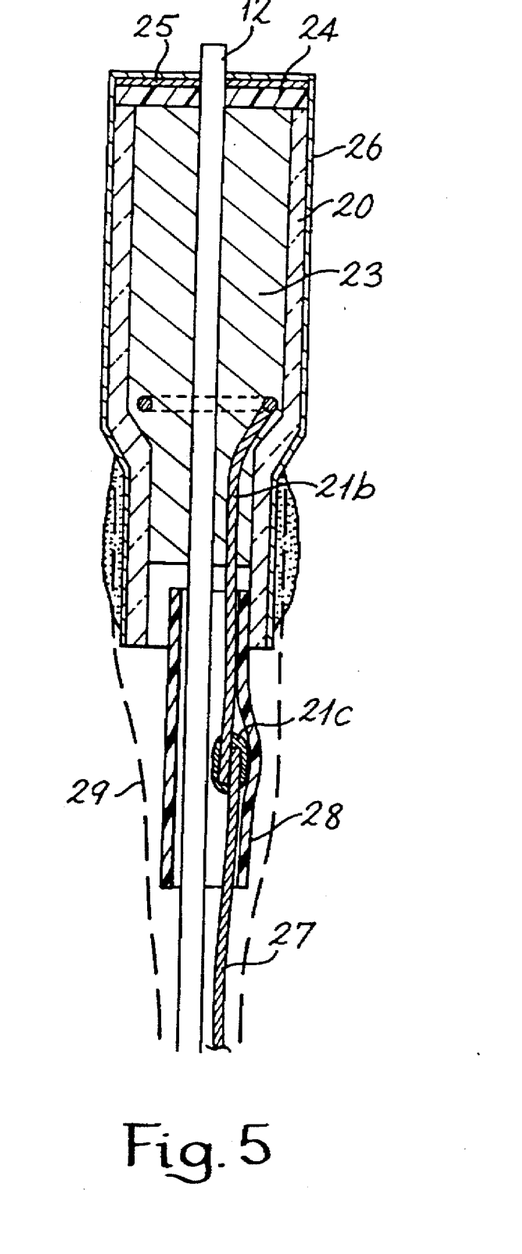
Figure 6:
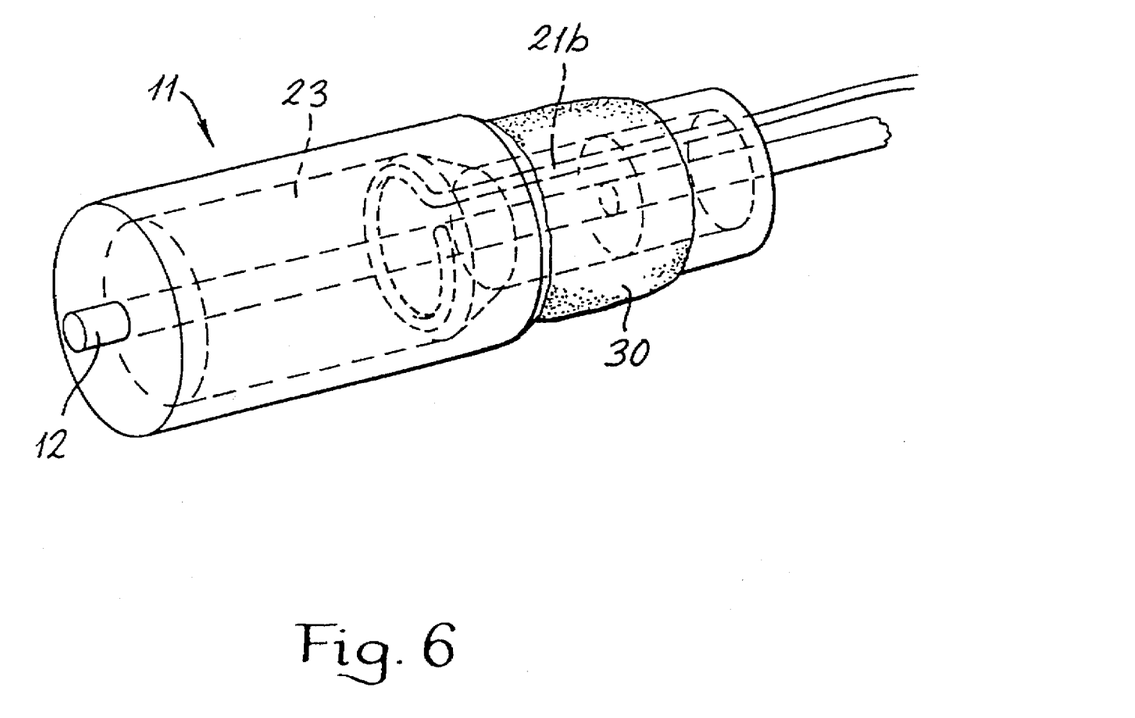
FIG. 6 is a phantom perspective view showing an electrical connection of the probe shown in FIG. 5.

The probe heads shown in FIGS. 4, 5 and 6, are similar to that shown in FIGS. 2 and 3, and corresponding parts are indicated by the same reference numerals. In the probe head shown in FIG. 4, however, the inner conductor 27 is bonded and electrically connected directly to the silver-loaded conductive epoxy plug 23, by means of a further added small body of silver-loaded conductive epoxy resin 21a, the conductive screw 21 of the head shown in FIG. 3 being omitted. In the head shown in FIGS. 5 and 6, the inner conductor 27 is conductively secured to one end of a copper wire conductor 21b by means of solder 21c, the other end of the conductor 21b being formed as a loop embedded in the silver-loaded epoxy plug 23 (as best seen in FIG. 6) and in good electrical connection therewith. In this case a shrunk-on heat-shrink sleeve 28 protects the soldered connection between the conductors 27 and 21b and provides insulation from the outer conductive sheath 29.

The above-described embodiments of the invention provide robust and constructionally simple forward-looking probe heads for use in investigating (and preferably also ablating) arterial blockages. Any of the above-described probe heads according to the invention may without difficulty be made with an outside diameter no greater than 3 mm, which is probably as small as will be required for medical purposes since such a probe may be used to investigate and ablate blockages in correspondingly small arterial vessels, and smaller vessels, if they become blocked, become bypassed in any event.

The use of piezoelectric polymeric material, in particular PVDF, rather than a piezoelectric ceramic, as the ultrasonic transducer is preferred for several reasons. First, PVDF provides a much better acoustic impedance match with body tissue or fluid than does a ceramic, and is a much better receiver of ultrasonic signals. Also, PVDF is inherently wideband in its frequency response because of its higher internal losses compared with piezoelectric ceramic materials, thereby tending to reduce the amount of ultrasonic wave reverberation within the transducer material and thereby tending to increase the resolution of the transducer. Furthermore, PVDF is robust rather than brittle, and is therefore well able to withstand ultrasound generated during high-power use of the probe to effect tissue ablation.

It will be understood that although in the illustrated probe heads the PVDF film 24 is metallised on only one surface, with reliance being placed on good all-over contact of its other surface with the conductive epoxy resin plug 23, this other surface of the film may also be metallised if desired to remove the necessity of good all-over contact (so long as care is taken to avoid short-circuiting to the film 25 or the paint layer 26). Also, instead of applying a pre-formed film 24, the film-form transducer element may be formed in situ by applying to the end of the plug 23 a solution of the PVDF polymer in a suitable solvent, spinning the device to remove excess, and heat-treating and subsequenty poling the coated polymer layer to render it piezoelectrically active.

It will also be understood that although the PVDF film 24, which may be some 10 μm in thickness, is shown as being flat it may be slightly dished (for example by slightly dishing the supporting end of the epoxy plug 23) in order to provide a focussing effect. Alternatively, as is described in UK Patent Specification No. 2212920, already referred to, a focusing effect may be obtained by dividing the PVDF film into electrically separate annular zones each of which generates its own signal, with due account being taken of phase differences between the signals; but, as will be recognised, this requires a separate electrical connection for each of the annular zones and would necessitate some redesign of the probe heads to provide such multiple connections.

For carrying out an ultrasonic examination by means of a probe according to the invention, the optical fibre in the cable 17 is fed via the connector 18 from a suitable laser source, which may conveniently be a conventional Q-switched Nd:YAG laser emitting pulses of 20 ns duration at a repetition frequency of, say, 50 Hz and a laser wavelength of 1.06 μm focused by a lens of, say, 4 cm focal length into one end of an optical fibre of which the other end is connected through the connector 18 to the optical fibre in the cable 17 and thus to the optical fibre 12. The output of the laser may be attenuated by the use of neutral density filters to such a level that the energy delivered by each laser pulse emitted from the exposed end of the optical fibre 12 is about 3 mJ. Pulses of this energy have been demonstrated as being quite adequate to excite a target surface into ultrasonic oscillation which is easily detectable by a transducer of the kind constituted by the PVDF film 12. The resulting electrical signals provided by the probe head 11 are processed in a known manner to provide ultrasonic imaging.

The same laser may be re-adjusted to provide a higher-energy output suitable for ablating the target, for example by switching the laser to operate in a normal mode instead of a Q-switch mode.

It will, however, be understood that alternative low and high laser energy levels may be achieved in other ways. At the target surface, the important parameter is power per unit area, and this can be varied by de-focussing the spot illuminated by the laser, either by altering the distance of the end of the optical fibre from the target surface, and/or by altering the optical system by which the laser output beam is fed to the optical fibre system. Alternatively, as indicated schematically in FIG. 1, the different laser power levels may be derived from two different lasers L1 and L2, possibly operating at different wavelengths, connected to respective optical fibre transmission systems which merge before reaching their common connection to the connector 18.

Figures 7, 8:
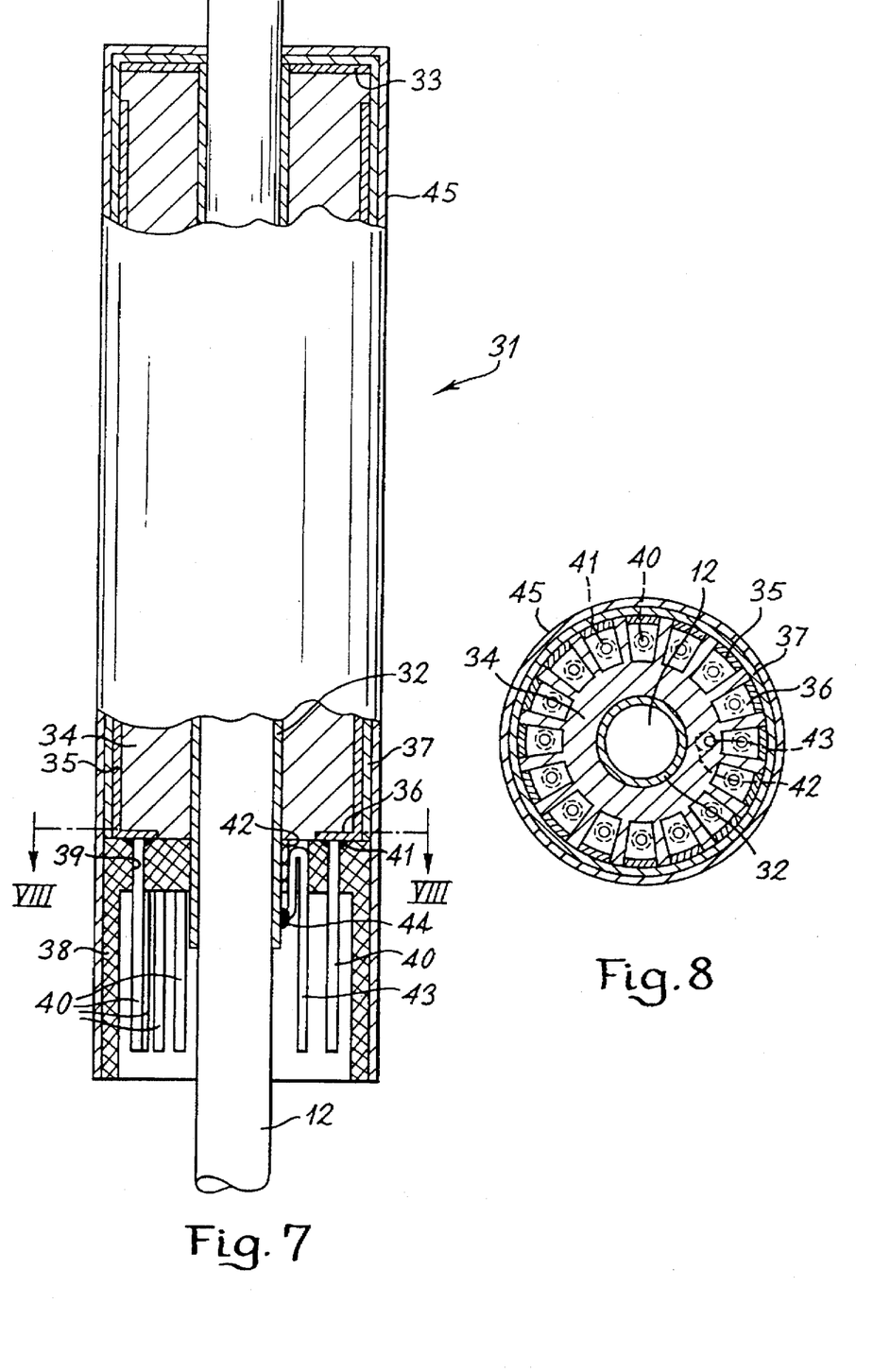
FIG. 7 is a longitudinal sectional view of another probe in accordance with the invention.
FIG. 8 is a cross-sectional view taken on the line VIII—VIII of FIG. 7.

FIGS. 7 and 8 illustrate a more elaborate probe head according to the invention which includes not only a forward-looking ultrasound receiving transducer element but also a plurality of sideways-looking transducer elements, all intended to receive ultrasound generated by a laser beam transmitted down an axial optical fibre 12. The probe head, indicated generally by the reference numeral 31, has an electrically conductive metallic central microtube 32 through which the optical fibre 12 extends, and surrounding the microtube 32 are an electrically conductive metal disc electrode 33 in electrical connection with it and an electrically insulating body 34, suitably of epoxy resin, along the outer periphery of which extend, in the axial direction, a plurality of electrodes 35. As shown in FIG. 8, the electrodes 35, which may be sixteen in number, are regularly distributed round the cylindrical periphery of the body 34. Each is spaced, and electrically insulated, at one end from the electrode 33, and at its other end terminates in a terminal section 36 which extends on an end face of the body 34. The electrodes 35 and their terminal sections 36, and also the electrode 33, may be preformed metal elements which are assembled in their intended positions relative to the microtube 32 prior to casting the epoxy resin body 34 between them, or they may be thin metallic films which are deposited by any convenient method on the body 34 after it has been formed.

The electrode 33, and the cylindrical peripheral surface of the body 34 and the associated electrodes 35, are coated with a continuous layer 37 of suitable piezoelectric polymer such as PVDF. As described above, this may be applied by a spin coating process in which PVDF is applied in a suitable solvent, the epoxy resin body 34 is rotated to obtain an even distribution of the applied layer, and the layer is then dried, heat treated and poled to render it piezoelectrically active. A terminal cap 38 is secured by means of a suitable adhesive to that end of the body 34 which is provided with the electrode terminations 36. The cap 38 is formed with a plurality of bores 39, each in register with a respective terminal section 36, for receiving a respective terminal wire 40 to connect electrically with the terminal section 36. The bores 39 are of enlarged diameter at their ends adjacent the terminal section 36, so that a small quantity of electrically conductive silver-loaded epoxy resin 41 inserted through each bore before fitting of the respective wire 40 may be forced by insertion of the wire into good contact both with the wire and with the adjacent termination section 36. The cap 38 has a further bore, 42, which accommodates a further terminal wire, 43, which is electrically connected, by solder or silver-loaded epoxy resin 44, to the microtube 32 and thus to the electrode 33.

Finally, the outer surface of the PVDF layer 37 is covered with a layer of silver-loaded electrically conductive paint 45, which also extends over the outer surface of the cap 38. It will be understood that, for use, the probe head 31 is secured on the end of a cable which (like the cable 13 described above) has the optical fibre 12 extending through it and has an electrically conductive outer sheath to which the conductive paint layer 45 is connected so as to constitute an extension of the electrical shielding provided by the cable sheath. In this case, the cable also includes seventeen signal conductor wires, of which one is connected to the terminal wire 43 and each of the others is connected to a respective one of the terminal wires 40, the signal conductor wires being enamelled or otherwise insulated from one another and connected at their other ends to respective pins of a multi-pin socket corresponding to the socket 16 shown in FIG. 1.

The layer 37 of piezoelectric polymeric material in the probe head 31 is continuous over the electrode 33 and all the electrodes 35, but each of its regions covering one of these electrodes, and sandwiched between that electrode and the overlying outer paint layer 45, terms an effectively separate ultrasonic transducer element, with substantially no cross-talk from one transducer element to another. It will be appreciated that although for purposes of illustration the layer 37 is shown as having substantial thickness, in practice its thickness may be only some 10 μm or less and lateral transmission of ultrasonic vibration (which in any case is quite heavily damped) is minimal. Thus the probe head 31 incorporates a forward-looking ultrasonic transducer element producing electrical output signals at the terminal wire 43, and a ring of sideways-looking transducer elements each producing electrical output signals at a respective one of the terminal wires 40. These transducer output signals, applied in known manner to appropriate signal processing equipment, enable an ultrasonic image of the surroundings of the probe head 31, both around and ahead of it, to be obtained.

As in the case of the probe head 11 shown in FIGS. 1 to 3, the optical fibre 12 of the probe head 31 is connected to receive and transmit a second laser beam of relatively higher average power sufficient to provide ablation of a target disposed ahead of the exposed end of the optical fibre 12, as well as a first laser beam of lower average power sufficient to generate ultrasound by means of which the target can first be investigated ultrasonically. As described above with reference to the probe head 11 shown in FIGS. 1 to 3, the ultrasound may be generated in the target itself by impingement of the first laser beam upon it, and in that case the ultrasound from the target impinges directly on the forward-looking transducer element constituted by the part of the layer 37 overlying the electrode 33 and indirectly, after reflection at any reflective boundary disposed laterally of the probe head, by any appropriate one or more of the sideways-looking transducer elements constituted by parts of the layer 37 overlying electrodes 35.

However, it is preferred, in the case of a probe provided with sideways-looking transducer elements as shown in FIGS. 7 and 8, to arrange that the source of the ultrasound shall be not the ultimate target for ablation but the medium immediately in front of the free end of the optical fibre 12. It is already established practice, when a probe of this kind is advanced along a blood vessel, to inject water or saline solution into the vessel so as to displace blood from the part of the vessel around and ahead of the probe head. If, as the laser L1 of FIG. 1, there is used an Er:YAG laser operating at a wavelength of 2.94 µm, at which water and saline solution are highly absorptive, suitable laser pulses from that laser emitted from the exposed end of the optical fibre 12 into the water or saline solution ahead of the fibre end are absorbed within a very short distance and generate ultrasound which is radiated laterally as well as forwards so as to be reflected by the vessel walls laterally of the probe head as well as by any obstruction or constriction ahead, so that both the sideways-looking and the forward-looking transducer elements produce electrical output signals which, after processing, provide an ultrasonically derived image of the vessel around and ahead of the probe head. This image may be used for positioning the probe head relative to the vessel walls and an obstruction ahead, before switching to the second laser L2 to provide a second laser beam at a wavelength for which the water or saline medium is transmissive and at a power level suitable for ablating the obstruction. It will be understood that although this choice of a suitable combination of laser wavelength and absorptive medium, to provide an essentially pulse-echo type of laser-generated ultrasonic probe, is especially preferred in the case of a probe with sideways-looking ultrasonic transducer elements (since it provides a well defined ultrasound source, in the medium immediately ahead of the probe, instead of a source at a variable distance ahead), it may also be employed in use of a probe which, like that shown in FIGS. 2 and 3, is only forward-looking.

Probes in accordance with the invention may, and preferably do, incorporate, in known manner, means for co-operating with guide wires to assist in steering the probe head along an artery; but, for simplicity and clarity of the disclosure of the invention, no such means or wires are illustrated in the accompanying drawings.

It will be appreciated that since, in a probe according to the invention, the ultrasonic signals are generated by laser irradiation, an ultrasonic transducer element in such a probe is required only to receive, and not to generate, ultrasound. Piezoelectric polymers are ideal materials for use to form the transducer elements in such a situation, since they have high "receive" sensitivity and, compared with conventional piezoelectric ceramic materials, are chemically more stable, mechanically more robust and acoustically better matched to water and blood. Due to their low dielectric permittivity, they have a large dielectric g constant, making them good ultrasonic receivers; furthermore, because of their high internal dielectric and mechanical losses, reception is intrinsically wide band.

It may be desirable that the laser L1, providing for the ultrasonic investigation, should be tunable over a range of laser wavelengths. In that case, this laser may be formed by an optical parametric oscillator, offering a wide range of tunability (from about 2 µm to 200 nm) and a wide range of laser pulse wavelengths. By such means, good discrimination may be obtained between healthy and diseased tissue; for example, at a wavelength of 308 nm, optical penetration depth in tissue is approximately 0.15 mm, permitting an ultrasound centre frequency of the order of 15 MHz, which may prove to be close to the optimum for laser probing. If it transpires that such is the case and a fixed laser wavelength of 308 nm is satisfactory, a compact XeCl excimer laser may be used instead as the laser source.

We claim:

1. A laser ultrasound probe suitable for intravascular use, comprising:

an ultrasonic transducer element comprising an ultrasound receiving surface formed of piazoelectric polymeric material; and an optical fibre having a first end directed forwardly from the ultrasound recieving surface and having a second end arranged to receive laser radiation for transmission therethrough, wherein the optical fibre is coupled with a laser source adapted to alternatively provide a relatively low average power laser beam at a first wavelegth, which, when modulated or pulsed and emitted from the first end of the optical fibre into a medium which is highly absorptive at the first wavelength, will cause said medium to generate and propagate ultrasound at an intensity suitable to be reflected by a target and recieve by the ultrasound receiving surface of the transducer element and converted thereby into electrical monitoring signals, and a relatively high average power laser beam at a second wavelength at which said medium is transmissive and suitable, when incident on the target, to produce ablation thereof, the ultrasonic transducer element being sufficiently robust to withstand the ultrasound which is then also generated.

2. A laser ultrasound probe as claimed in claim 1, in which the target is connected by the medium in which the ultrasound is generated.

3. A laser ultrasound probe as claimed in claim 1 or claim 2, wherein the first end of the optical fibre projects through and forwardly from the ultrasound receiving surface.

4. A laser ultrasound probe as claimed in claim 1 or claim 2, wherein the first end of the optical fibre is directed in a forward longitudinal direction of the probe and the ultrasonic transducer element is a forward-looking transducer element of the probe, susceptible to ultrasound generated and propagated forwardly in the medium and reflected by a first target located in the forward direction, and the probe is further provided with at least one sideways-looking ultrasonic transducer element susceptible to ultrasound generated and propagated in the medium and reflected by a second target contacted by the medium and disposed laterally of the probe.

5. A laser ultrasound probe as claimed in claim 4 and provided with a plurality of sideways-looking transducer elements, disposed circumferentially round the probe, each said transducer element having its own electrical output-signal connection for connection to a signal processing apparatus for image derivation.

6. A laser ultrasound probe as claimed in claim 5, wherein said probe is provided with sixteen sideways-looking transducer elements.

* * * * *